United States Patent [19]

Abbott

[11] Patent Number: 4,840,542
[45] Date of Patent: Jun. 20, 1989

[54] INFUSION PUMP WITH DIRECT PRESSURE SENSING

[75] Inventor: Martyn S. Abbott, Richardson, Tex.

[73] Assignee: Quest Medical, Inc., Carrollton, Tex.

[21] Appl. No.: 37,019

[22] Filed: Apr. 10, 1987

Related U.S. Application Data

[63] Continuation-in-part of Ser. No. 717,131, Mar. 27, 1985, Pat. No. 4,657,490.

[51] Int. Cl.$^4$ .......................... F04B 43/08; A61M 1/00
[52] U.S. Cl. ................................ 417/9; 417/28; 417/479
[58] Field of Search .................... 417/28, 63, 317, 478, 417/479, 9, 43, 44; 604/153, 152

[56] References Cited

U.S. PATENT DOCUMENTS

| | | | |
|---|---|---|---|
| 9,107 | 7/1852 | Ware | 92/101 |
| 936,089 | 10/1909 | Wise et al. | 417/244 |
| 1,305,603 | 6/1919 | Hodgson | 92/101 |
| 1,338,081 | 4/1921 | Hodgson | 92/101 |
| 2,961,965 | 11/1960 | Senning et al. | |
| 4,199,307 | 4/1980 | Jassawalla | 417/474 |
| 4,236,880 | 12/1980 | Archibald | 417/63 X |
| 4,256,437 | 3/1981 | Brown | 417/45 |
| 4,273,121 | 6/1981 | Jassawalla | 128/214 F |
| 4,276,004 | 6/1981 | Hahn | 604/153 |
| 4,277,226 | 7/1981 | Archibald | 604/153 |
| 4,321,014 | 3/1982 | Eburn, Jr. et al. | 417/317 X |
| 4,322,201 | 3/1982 | Archibald | 417/279 |
| 4,335,835 | 6/1982 | Biegler et al. | 222/95 |
| 4,461,222 | 8/1984 | Lundquist | 417/360 X |
| 4,479,706 | 10/1984 | Bilstad | 604/153 |
| 4,548,607 | 10/1985 | Harris | 604/153 |
| 4,696,671 | 9/1987 | Epstein et al. | 604/56 |

FOREIGN PATENT DOCUMENTS

| | | | |
|---|---|---|---|
| 1911919 | 3/1969 | Fed. Rep. of Germany . | |
| 201375 | 11/1936 | Switzerland | 92/101 |
| 2053378 | 2/1981 | United Kingdom . | |

Primary Examiner—Leonard E. Smith
Attorney, Agent, or Firm—Richards, Harris, Medlock & Andrews

[57] ABSTRACT

An infusion pump incorporates a cassette formed by bonding of two substantially flat sheets. The fluid to be infused to the patient comes into contact only with the cassette. The cassette includes first and second flexible sheets which define a pumping chamber therebetween. The infusion pump is provided with a pumping member having a hub and a plurality of petal-shaped sections extending radially outward therefrom and pivotal relative thereto. A stepping motor can be operated to move the pumping member against the second flexible sheet to decrease the volume of the pumping chamber and pump fluid to the patient. A load cell monitors the force exerted by the stepping motor on the hub. An outlet restriction value is electronically controlled by a second stepping motor in response to the pressure sensed by the load cell to control pumping to a predetermined pressure. The pressure can be selectively varied which permits the use of a low pressure at low flow rates to decrease the time necessary to detect an occlusion in the output lines.

2 Claims, 7 Drawing Sheets

INFUSION PUMP WITH DIRECT PRESSURE SENSING

RELATED APPLICATION

This application is a continuation-in-part of U.S. Pat. Application Ser. No. 06/717,131, filed Mar. 27, 1985, new U.S. Pat. No. 4,657,490.

TECHNICAL FIELD

This invention relates to the delivery of a fluid to a patient by pressurizing the fluid, and in particular to delivery by an infusion pump which incorporates an inexpensive disposable cassette.

BACKGROUND OF THE INVENTION

Infusion of fluids, such as drugs and plasma, into a patient is commonplace in the medical field. Two common infusion methods are intravenous delivery of fluids by gravity and either intravenous or intraarterial delivery by actually pumping the fluids for delivery to the patient.

In pump delivery, an infusion pump is used to pressurize the fluid. Past devices often require a complex cassette mechanism which comes into direct contact with the fluid to be delivered.

However, peristaltic pumps acting upon in-line tubing segments have been used in this art. One example of a peristaltic pump, disclosed in U.S. Pat. No. 4,155,362, includes a back pressure valve to prevent gravity siphoning from the pumping chamber.

Another relatively simple pumping arrangement is disclosed in U.S. Pat. No. 4,142,524, in which a casette is provided with inlet and outlet valves to and from a pumping chamber. The pump presses a rubber diaphragm on the cassette to diminish the volume of the casette chamber by a known amount to deliver a predetermined quantity per pump stroke. An even simpler disposable element is disclosed in the pumping arrangement of U.S. Pat. No. 4,199,307, in which a pancake-shaped resilient pumping chamber is provided with upper and lower valves and an activating pumping piston which displaces a known volume on the pumping stroke. Yet another pump approach is disclosed in U.S. Pat. No. 4,322,201, which seeks to provide continuous, uninterrupted fluid flow by alternating between two pumping chambers, each of which employs the principle of the rolling diaphragm. A third rolling diaphragm chamber is employed for mechanically sensing pressure within the device for control purposes.

None of the foregoing art, however, possesses the advantages of the present invention in providing an extremely simple disposable element in combination with a relatively straightforward pumping action which is accurate and which provides sound and reliable pressure monitoring and self-checking diagnostics.

SUMMARY OF THE INVENTION

In accordance with one aspect of the present invention, an infusion pump is provided for pumping a fluid to a patient for infusion. The pump includes a disposable cassette having first and second flat flexible sheets defining a pump chamber within the cassette, the pump chamber being variable in volume as fluid fills the chamber or is pushed from it, the disposable cassette further having an inlet passage for movement of fluid into the pump chamber and an outlet passage for movement of the fluid out of the pump chamber. Means are provided for confining movement of the outer surface of the first sheet; and a pumping member is provided for contacting the outer surface of the second sheet to deform the sheet between the pumping member and the confining means to decrease the volume of the pump chamber and pump the fluid from the pumping chamber. The pumping member includes a center hub section and individual petal-shaped sections pivotally attached to the hub and extending radially outward from the hub. Means are provided for supporting each of the petal-shaped sections at their remote ends for pivotal motion about an axis generally parallel to the axis of pivotal motion between each petal-shaped section and the hub. Means are provided for urging the hub against the outer surface of the second sheet with the petal-shaped sections pivoting about the axes and also being urged against the second sheet. Substantially the entire surface area of the second sheet is contacted by the hub and petal-shaped sections to decrease the volume of the pumping chamber and pump the fluid therefrom.

In accordance with another aspect of the present invention, the structure for confining the first sheet comprises a concave curved surface of constant radius against which the outer surface of the first sheet is confined. Also, an inlet valve can be provided for opening and closing the inlet passage in the cassette and a delivery valve is provided for closing the outlet passage to a variable orifice size so that the valve opens to permit fluid flow from the pump chamber past the outlet valve when the movement of the pump piston pressurizes the fluid in the pumping chamber to a predetermined pressure. The outlet valve can be electronically controlled to allow the pressure in the pump chamber to be automatically controlled in a predetermined manner, as by controlling it to a constant pressure level selected by the user. A load cell may be used to measure the fluid pressure in the pump chamber and can detect a lack of fluid, valve failure and occlusions. The load cell may be used to detect occlusions by determining that pumping pressures exceed a limit selected by the user.

In another mode of operation, the occlusion pressure limit may be established automatically using the load cell to set a limiting pressure based on the gravity head pressure of the I.V. container hanging above the pump chamber. In this mode, prior to commencing pumping, the delivery valve is closed and the flow channel opened above the pump chamber. The pumping means is advanced against the pump chamber and the load cell force measurement then is reflecting the gravity head above the pump channel. This measurement is then used to establish the operational occlusion pressure limit.

In accordance with another aspect of the present invention, the disposable cassette is provided with a quick-fill supply chamber upstream from the pumping chamber. An inlet passage is provided for movement of fluid into the supply chamber and a valve supply transfer passage is provided for movement of the fluid from the supply chamber to the pump chamber.

BRIEF DESCRIPTION OF THE DRAWINGS

A more complete understanding of the invention may be had by reference to the following Detailed Description when taken in conjunction with the accompanying Drawings, wherein.

DETAILED DESCRIPTION

Figure 1:
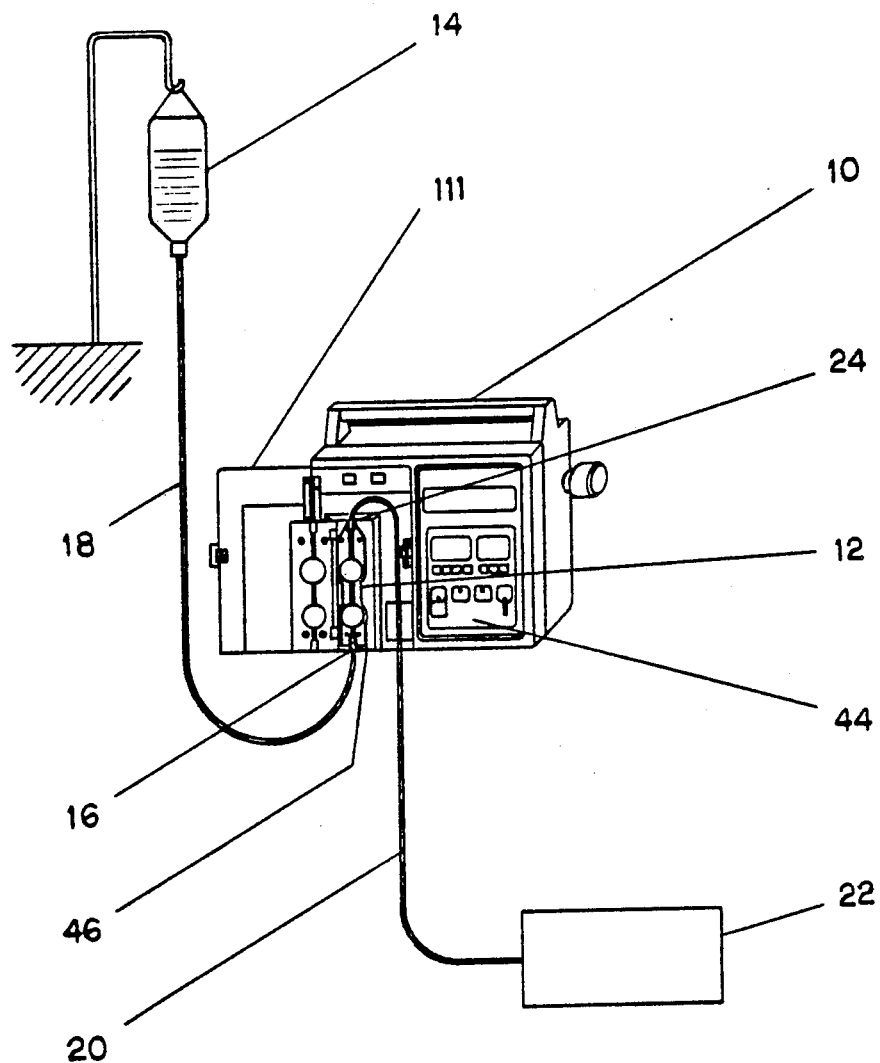
FIG. 1 is a schematic representation of an infusion pump forming one embodiment of the present invention.

As illustrated in FIG. 1, the pumping system is composed of an instrument 10 in which a disposable cassette 12 is mounted for operation. Supply container 14 containing the fluid to be infused is connected to inlet 16 of the cassette 12 by means of tubing 18. Outlet tubing 20 extends to the patient 22 from the outlet 24 of cassette 12.

Figures 4, 5:
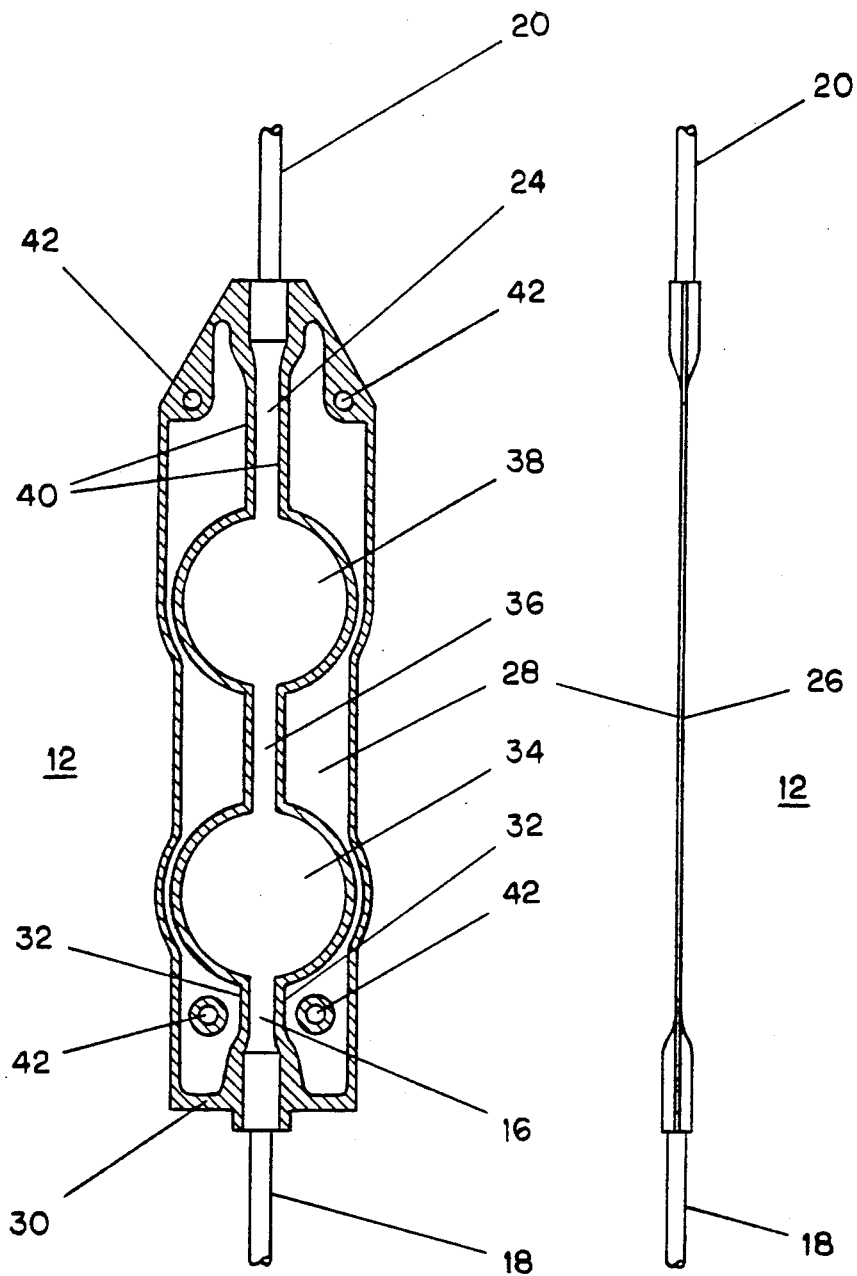
FIG. 4 is a front view of the disposable cassette.
FIG. 5 is a side view of the disposable cassette.

Cassette 12, as best seen in FIGS. 4 and 5, is formed by a first flexible sheet 26 and a second flexible sheet 28, which may be formed from a suitable flexible sheet material, such as polyvinyl chloride. The cassette 12 may be assembled by bonding sheets 26 and 28 over a selected bonding area 30 indicated by hatching in FIG. 4. The bonding area 30 includes bonding along spaced parallel lines 32 in order to form a cassette inlet passage 16 extending from one end of the cassette between sheets 26 and 28. Inlet passage 16 extends to a supply chamber 34 having a generally circular configuration. A transfer passage 36 extends from the side of supply chamber 34 opposite inlet passage 16, communicating with a pump chamber 38. Bonding along two parallel lines 40, extending from pump chamber 38 forms outlet passage 24.

Thus, there is provided longitudinally through the central area of cassette 12, a continuous fluid path extending from inlet 16 through supply chamber 34, transfer passage 36, and pump chamber 38 to the cassette outlet 24. Supply tube 18 is inserted into inlet passage 16 and bonded by any suitable means, such as by solvent bonding. Likewise, patient tube 20 is inserted into outlet passage 24 and bonded thereto. In the preferred form of the invention, the cassette is, as shown in FIG. 5, essentially flat. This permits production of the cassette from flat sheet without the necessity of any forming operation. Depending upon the material used for sheets 26 and 28, it may be desirable to provide slight relief by vacuum forming in one or both of the sheets along the open flow path formed by the cassette, in order to minimize adhesion of the unbonded areas during storage.

The flexibility of the cassette must be sufficient that, with fluid at a relatively low pressure being provided at the inlet 16, with the outlet 24 closed, fluid will flow into the cassette filling it and causing the chamber 34 and 38 to bulge with fluid by stretching of the sheets 26 and 28. Four mounting holes 42 are provided in the margins of the cassette for positioning and mounting of the cassette in the instrument 10.

Figure 2:
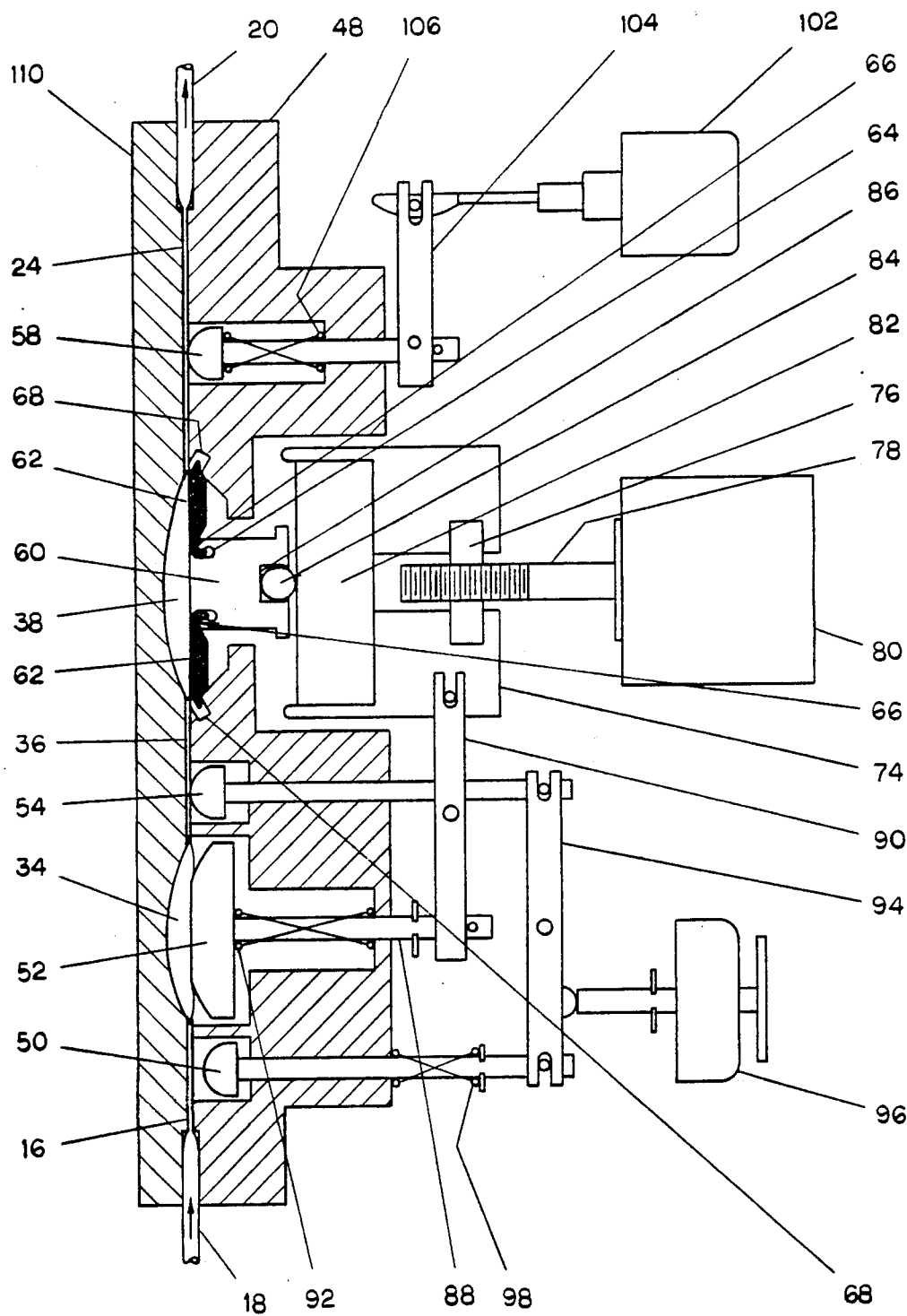
FIG. 2 is a cross-sectional view of the infusion pump in FIG. 1.
Figure 3:
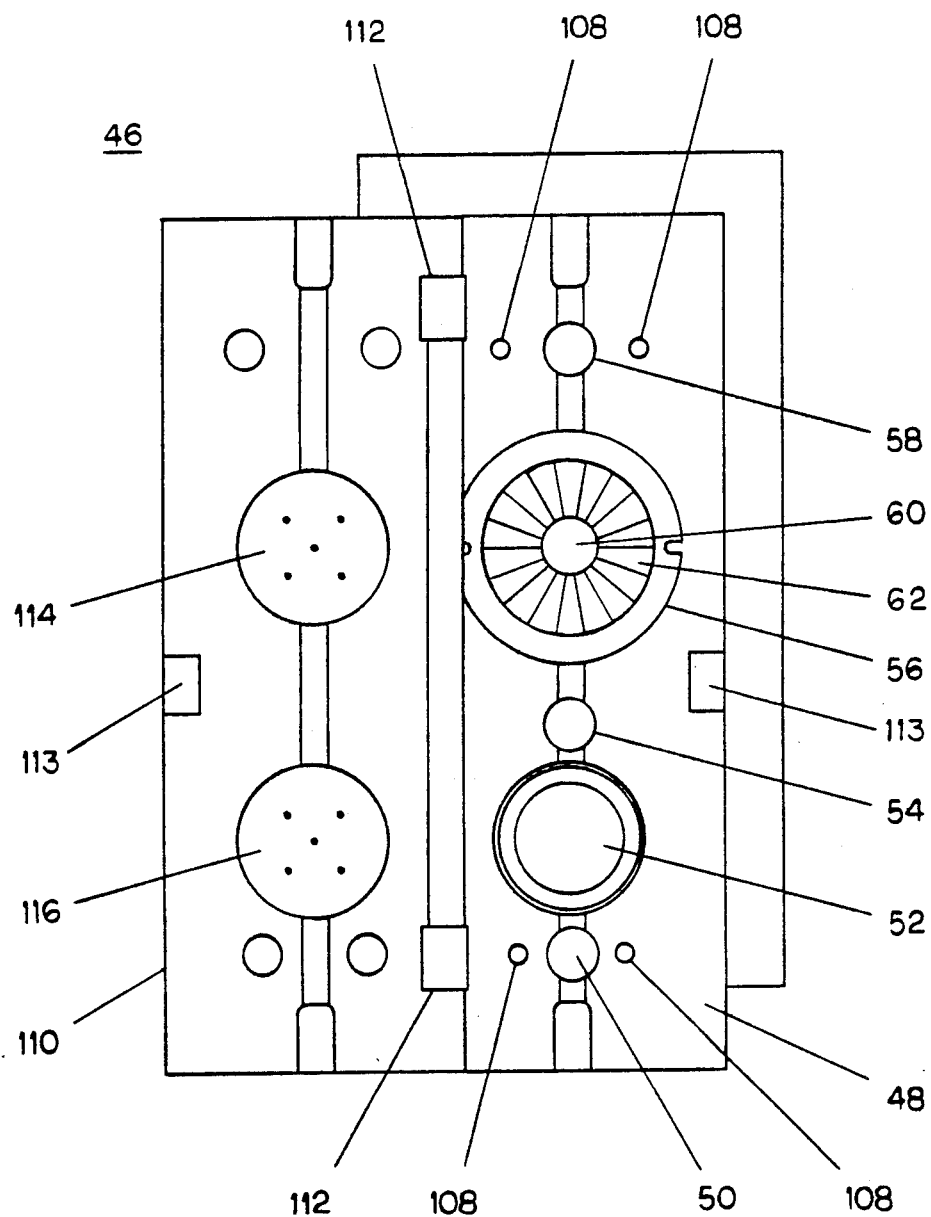
FIG. 3 is a front view of the pump prior to mounting the disposable cassette.

The front panel of the instrument body is functionally divided into a data display/operator input panel 44 and a cassette receiving and actuating section 46, which is concealed behind one or more doors (not shown in FIG. 1). The details of construction of the cassette receiver/actuator section 46 are best illustrated in FIGS. 2 and 3. The moving members which operate upon cassette 12 when it is in operating position are arrayed on panel 48 secured to the instrument body. Proceeding from upstream, the major elements are: inlet valve 50, refill pressure member 52, transfer valve 54, petal assembly pumping member 56, and delivery valve 58.

Figure 6:
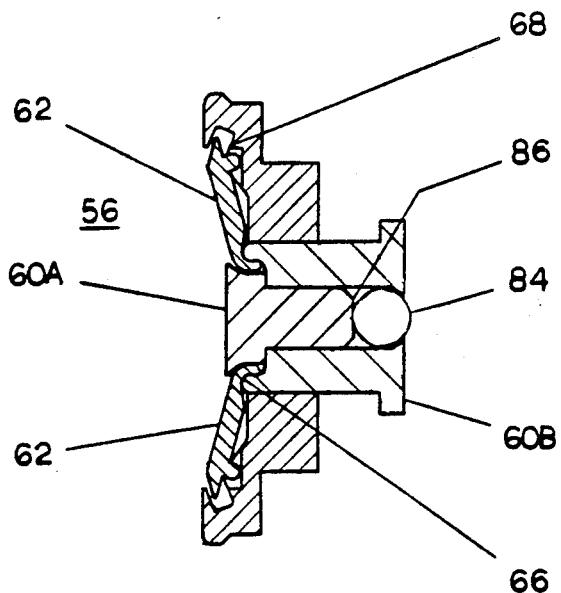
FIG. 6 is a partial cross-sectional view of the pumping member shown in the retracted position.
Figure 7:
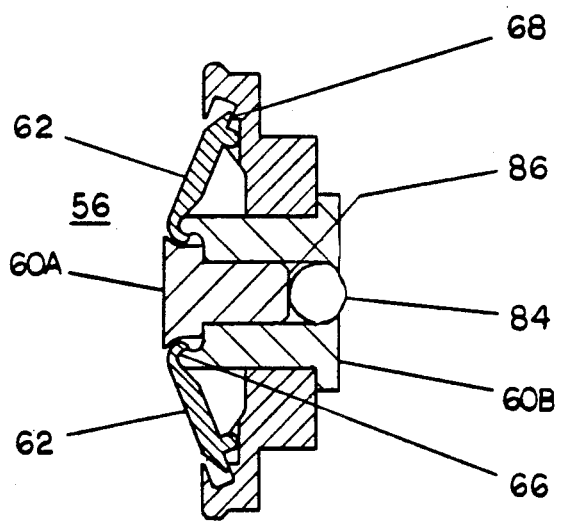
FIG. 7 is a partial cross-sectional view showing the pumping member of the infusion pump in the extended position.

Petal assembly 56 includes a central hub 60 surrounded by a plurality of petal shaped sections 62 to form the movable pressing surface which produces pumping pressure in the device. As best shown in FIGS. 6 and 7, the hub 60 is formed by press fit of male hub member 60a and female hub member 60b. A circular recess 64 near the outer edge of hub 60 is formed between the two hub members. Each petal section 62 is provided on the rear face of its inner end with a smooth hooked-shape curve portion 66 which corresponds to a smooth curve provided on the hub recess 64. The inner end of each petal section 62 is pivotally retained in the hub recess 64, with the complimentary smooth curves of each member permitting relative pivotal movement of each petal shaped section with respect to the hub about an axis adjacent recess 64. The instrument body panel 48 is provided with an annular petal nest 68 that circumferentially surrounds hub 60 and retains the outer end of each petal shaped section 62. The confronting surfaces of petal nest recess 68 and the outer end of each petal shaped section 62 are also shaped for smooth pivoting of the petal shaped sections with respect to the instrument body about an axis adjacent the nest 68.

A movable carriage 74 is mounted behind hub 60, and carries a drive nut 76 which is engaged with the threads of a threaded motor shaft 78 rotated by stepper motor 80. The forward end of carriage 74 is recessed to receive a load cell 82. Load cell 82 has its central force-measuring diaphragm confronting a metal ball 84 retained in a rear central recess 86 formed on hub 60. Thus, rotation of stepper motor 80 acts, through the cooperation of threaded motor shaft 78 and carriage nut 76 to drive carriage 74 forward. This action transmits force through load cell 82 and metal ball 84 to hub 60, moving the hub forward. The translational motion of hub 60 also causes each petal shaped section 62 to pivot near each of its ends. The petal assembly thus forms a truncated cone of varying height as the hub moves between the extreme positions illustrated in FIGS. 6 and 7.

Refill pressure member 52 is carried at the forward end of refill shaft 88, which is driven either forwardly or rearwardly through lever 90 acted upon by the carriage 74. Thus, as viewed in FIG. 2, when carriage 74 is moving forwardly to push the petal assembly 56 forward, the action of refill lever 90 causes shaft 88 and refill pressure member 52 to be withdrawn. As motor 18 is driven in the opposite direction to withdraw carriage 74, lever 90 allows the refill pressure member 52 to move forward. Spring 92 biases refill pressure member 52 to its forward position, and thus carriage 74 to the rearward direction.

Inlet valve 50 and transfer valve 54 have rounded surfaces for engaging the flow path of the cassette, and are operated in tandem fashion through inlet valve lever 94 driven by solenoid 96. When one of the two valves is in the open or rearward position, the other is necessarily in the closed or forward position. Preferably, the parts are assembled so that in the middle of the path of travel of valve lever 94, both valves are closed to ensure no by-passing of fluid. Bias to inlet valve lever 94 is provided by spring 98 surrounding the inlet valve shaft, which biases the arrangement to the condition of inlet valve open, transfer valve closed.

Delivery valve 58 is operated by a stepper motor 102 acting through delivery valve lever 104, and is biased to the closed position by spring 106. The linear stepper motor 102 is capable of positioning the delivery restriction valve 58 in any position from fully retracted or open position, as shown, to a fully extended or closed position.

Actuator panel 48 is provided with mounting pins 108 corresponding to the mounting holes 42 in cassette 12. An actuator door 110 is mounted to panel 48 by hinges 112 and is closed by latch 113. Although not shown in FIG. 3, a second outer door 111 (FIG. 1) is preferably used to enclose door 110. As a double check for patient safety, opening of this outer door 111 would stop pumping and sound an alarm. In the inner face of door 110, concave depression 114 is arranged to confront petal assembly 56 when the door is closed, and similar concave depression 116 confronts the refill pressure member 52. Depressions 114 and 116 are provided with air vent holes through the front of the door to facilitate closing of the door with the cassette 12 in position. With the cassette mounted on pins 43, the pump chamber 38 of the cassette is captured between petal assembly 56 and door depression 114. The supply chamber 34 is likewise captured between pressure member 52 and door depression 116. In the operating position, valve 50 is adjacent inlet passage 16 to close off the inlet when valve member 50 is extended. Likewise, valve 54 may be activated to close off transfer passage 36. The delivery valve 50 may be activated to selectively close outlet 24 of cassette 12, to an orifice of any desired size. The pumping compartment defined between the rigid wall of depression 114 and the petal assembly 56 must be completely filled by the fluid filled pump chamber 38 when the petal assembly 56 is in its retracted position illustrated in FIG. 6, and the pump chamber 38 is bulged with fluid at a low fluid pressure of approximately 10 inches of water. The volumetricity of pumping is then provided by the accuracy of volume displaced between the extreme positions of the petal assembly 56 illustrated in FIGS. 6 and 7, and the compliance of sheet 28 to the moving truncated cone surface presented by the petal assembly 56.

Since the material used to construct the cassette is flexible it conforms to the surface of the petal elements so that the position of the petal assembly defines the volume of fluid enclosed between it and the hemispherical surface on the other side very precisely. This enables the volumetric performance of this arrangement to be defined almost completely by the movement of the hub, and thus of the petal shaped sections, and not by the mechanical properties of the disposable element. The volume displaced by the petal assembly varies in a linear fashion with the translational movement of hub 60.

Figure 11:
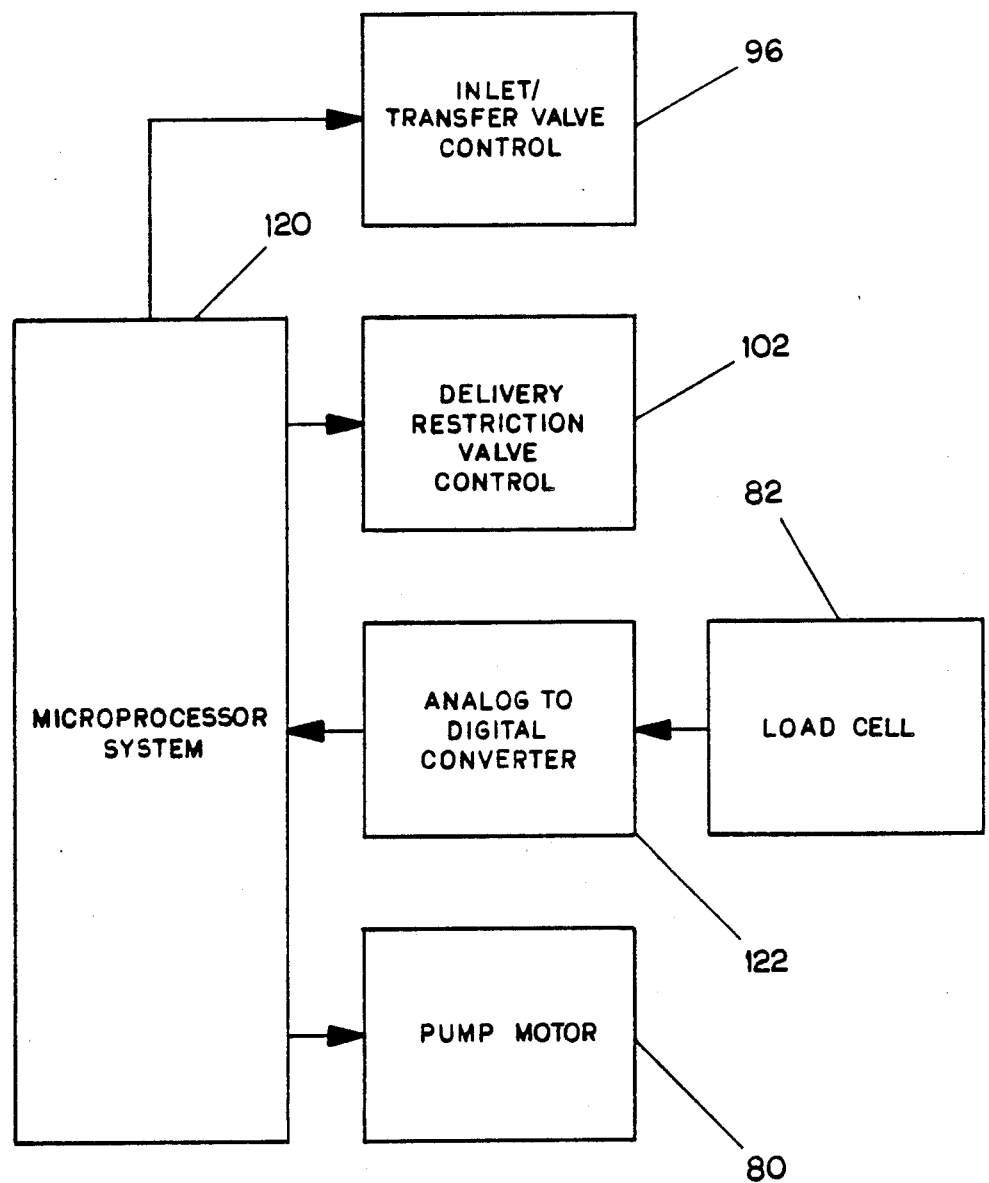
FIG. 11 is a schematic of the electronic controls within the infusion pump.

As illustrated in FIG. 11, the system is operated under the control of a microprocessor system 120. The microprocessor, as illustrated in FIG. 11, controls the movement of solenoid 96 between its two positions: (1) inlet valve open, transfer valve closed, and (2) inlet valve closed, transfer valve open. Likewise, microprocessor 120 controls delivery valve stepper motor 102 to select the total or partial restriction imposed by delivery valve 58 on the cassette outlet 24. Microprocessor 120 also selects, in accordance with the rate selected by the operator on input panel 44, the rate of movement of the pumping stepper motor 80. Continuous control over operation, and diagnostics for abberant conditions, are principally provided by load cell 82 which directly measures the force being exerted on the pump chamber 38 by petal assembly 56. This data is continuously provided to microprocessor 120 through A/D converter 122.

Figure 8:
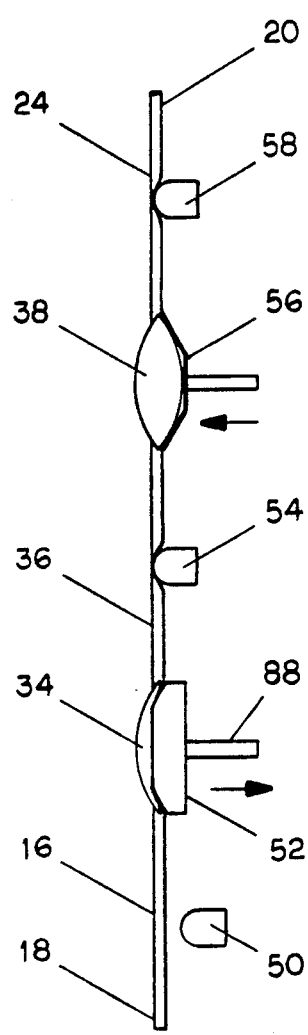
FIGS. 8, 9 and 10 illustrate schematically the operational sequence of the infusion pump.
Figure 9:
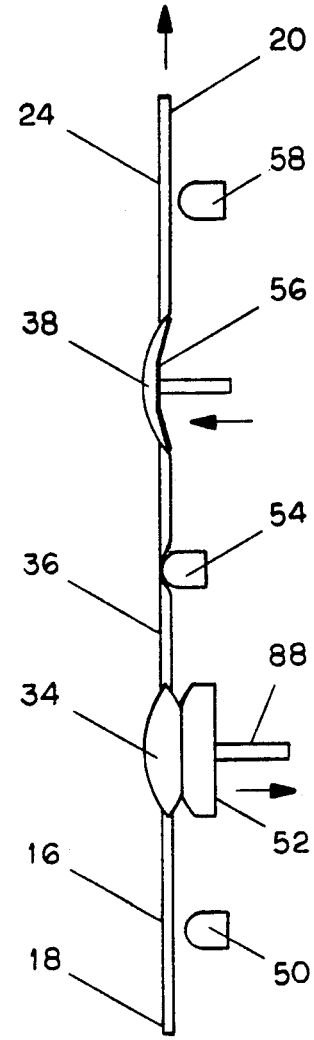
Figure 10:
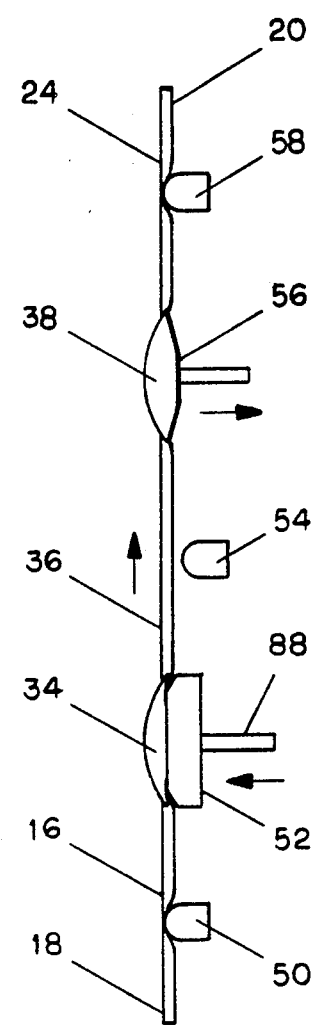

A typical cycle of operation is illustrated in FIGS. 8 through 10. FIG. 8 illustrates the condition of the actuator and disposable as the delivery portion of the cycle has begun. At this stage, the pump chamber 38 has been completely filled with fluid to occupy the compartment with petal assembly 56 fully retracted. Delivery valve 58 and transfer valve 54 are closed, completely capturing the fluid in pump chamber 38. Inlet valve 50 is opened, so that fluid may enter the supply chamber 34 as refill pressure member 52 is retracted. In this initial stage, the microprocessor begins the initial stage of the delivery cycle by directing the pump chamber stepper motor 80 to advance to begin pressurization of the fluid in pump chamber 38. During the first few steps of operation, valves 58 and 54 remain closed to permit this initial pressurization. Elevation of the force required to advance the petal assembly 56 is sensed by load cell 82 which data is fed to the microprocessor 120. This state serves as a diagnostic to verify the capturing of a full load of fluid in the pump chamber 38. A failure to pressurize in the first several steps of motor 80 indicates a system problem. It could be that the fluid supply is depleted, so that the pump chamber 38 has not been filled, or that the supply container 14 is at an inadequate height to cause the gravity fill into inlet 16 of the cassette. A third possibility is that a valve defect in valve 54 or 58 is permitting fluid to leak from the chamber 38. In any of these events, operation of the instrument will be stopped by the microprocessor 120 and an alarm sounded.

If, however, normal pressurization occurs, microprocessor 120 instructs delivery valve 58 to open as motor 80 advances, to deliver fluid to the patient through outlet 24, as illustrated in FIG. 9. Continuous monitoring of load cell 82 permits the microprocessor to exercise continuous control over delivery valve 58 to selectively restrict the outlet 24. This permits the device to ensure that gravity siphoning at a higher rate than the requested rate does not occur. The microprocessor is also programmed with a selected maximum pressure limit set by the user through display/input panel 44, which is used in the continuous pressure monitoring. Escalation of pressure above the selected maximum pressure, even with the delivery valve 58 wide open, will result in alarm and shutdown of the instrument, indicating that there is some occlusion which requires nursing attention, and that fluid is not reaching the patient. The ability to select a maximum pressure limit by the user permits relatively rapid occlusion alarms, even at relatively low selected infusion rates.

Preferably, the microprocessor is programmed to maintain a relatively constant pressure in pump chamber 38 by selective restriction of delivery valve 58, such constant pressure being just below the maximum pumping pressure selected by the operator. This is helpful in ensuring that there are no variations in volumetric delivery which might result from operation at varying pumping pressures.

While fluid is being delivered by advancement of the petal assembly 56, the refill pressure member 52 is automatically being withdrawn, and fluid is entering the supply chamber 34 through open inlet 16. When petal assembly 56 has reached its fully extended position, illustrated in FIG. 7, valves 50 and 58 close, and valve 54 opens. Microprocessor 120 then reverses stepper motor 80 for a rapid retraction of petal assembly 56 and a rapid extension of refill pressure member 52 as illustrated in FIG. 10. This permits a very quick transfer of fluid into pump chamber 38 which will arm the device for the next delivery cycle. During the pumping portion of the delivery cycle energy was stored in the spring 92 immediately behind the refill pressure member 52. This energy is used to effect the transfer of fluid so as to drastically reduce the mechanical loading on the main pump motor. The purpose of this is to allow an increased motor speed during the fluid transfer step which in turn reduces the time taken to effect the transfer as it is principally limited only by the maximum operating speed of the main pump motor 80. Once the transfer of fluid is complete valve 50 opens and valve 54 closes and the system is in the condition once more indicated in FIG. 8. A mechanical stop on shaft 88 limits the amount of movement of the refill piston 52 so as to avoid pumping any fluid back towards the fluid container 14 as valve 50 opens.

It will be appreciated that the cassette and instrument could be designed without supply chamber 34, refill pressure member 52, and transfer valve 54, but in that event the refill cycle time would be dependent upon the rate of flow into pump chamber 38 dictated by natural forces of gravity. Use of the device in the form illustrated permits the instrument to control the time taken up by the refilling of pump chamber 38, and to cause that step to happen rapidly to limit the duration of the refilling cycle.

In another mode of operation, the occlusion pressure limit may be established automatically based upon the height of the I.V. container above the pump. If the load cell 82 is used to accomplish this function, independent operation of the inlet valve 50 and transfer valve 54 is required. Valves 50 and 54 would both be opened and the restriction valve 58 would be closed prior to commencing each pump cycle. The pumping motor 80 is advanced so that the load cell 82 can measure the upstream fluid head pressure. The transfer valve 54 would then close and a normal pump cycle continue using the fluid head pressure reading to calculate the operating occlusion pressure, either as a fixed percentage of the fluid head pressure or as some other function of the fluid head pressure. If the occlusion pressure is exceeded during operation, pumping is stopped and an alarm given just as in the case where the occlusion pressure is set by the user. Alternatively, without independent control of these valves, a pressure measuring means may be incorporated adjacent the refill chamber 34. Such a means may consist of a spring loaded piston and a position measuring transducer at the refill chamber 34. Whether using the load cell 82 or other pressure sensing means, the gravity head pressure of the I.V. fluid container 14 may be used to establish the occlusion pressure limit. If a higher or lower occlusion pressure is desired, the I.V. container 14 may be raised or lowered by the user.

Although specific embodiments of the invention have been illustrated in the accompanying drawings and described in the foregoing detailed description, it will be understood that the invention is not limited to the embodiments disclosed, but is capable of numerous rearrangements, modifications and substitutions of parts and elements without departing from the spirit of the invention.

I claim:

1. A pump for parenteral administration of fluid to a patient from an elevated I.V. container comprising:
   tubing extending from the I.V. container to the patient;
   a disposable pump chamber in line with the tubing;
   a pump including means operating in discrete cycles for pressurizing the pump chamber and means for measuring the pressure during pumping cycles;
   an outlet valve downstream from the pumping chamber;
   means for measuring the gravity head pressure at the pump when the outlet valve is closed prior to the beginning of a pumping cycle, and establishing an operational occlusion pressure based on the measured head; and
   means for stopping the pump if the measured pumping pressure exceeds the occlusion pressure during a pumping cycle.

2. An infusion pump for pumping a fluid to a patient comprising:
   a disposable cassette formed of first and second flexible sheets bonded together to define a pumping chamber and a supply chamber with an inlet passage entering the supply chamber, an intermediate passage connecting the supply chamber and pumping chamber and an outlet passage from the pumping chamber;
   a frame for supporting the disposable cassette having a first surface for confining motion of the first sheet, the surface confining the first sheet having a generally concave shape of constant radius;
   a pump assembly mounted on the structure for contacting the outer surface of the second sheet and for urging the second sheet toward the first surface to decrease the volume of the pumping chamber and pressurize the fluid therein, the pump assembly including a hub and a plurality of wedge-shaped petal sections extending radially outward from the hub in pivotal relationship thereto, the radially outermost end of each of the petal-shaped sections being pivotally mounted on the frame, the center section and petal-shaped sections defining a surface for contacting the exterior of the second sheet;
   a piston shaft mounted to the center section for linear motion in a first direction to urge the center section and petal-shaped sections against the second sheet;
   a load cell mounted on the piston shaft for measuring force exerted on the hub through the piston shaft;
   a stepping motor connected to the piston shaft through the load cell for exerting force on the piston shaft;
   delivery valve for varying the cross section of the outlet passage between closure of the passage and the open undeformed cross section of the outlet passage;
   means for operating said delivery valve in response to the force exerted on the center section through the piston shaft measured by the load cell for causing fluid to be pumped from the pressure chamber at a predetermined pump pressure;

a transfer valve for closing and opening the intermediate passage between the supply chamber and the pumping chamber;
an inlet valve for opening and closing the inlet passage to the supply chamber; and
microprocessor controlled means for electronically causing the stepping motor to move the piston assembly in the first direction with the intermediate valve and output restriction valve closing the intermediate and outlet passages for generating an alarm if the fluid pressure in the pumping chamber does not rise within a predetermined movement to indicate an instrument defect, said microprocessor controlled means upon sensing an increase in the fluid pressure continuing to direct the stepping motor to move the piston assembly in the first direction and controlling said means for operating the delivery valve to pump fluid from the pump chamber at the predetermined pump pressure to the patient with the transfer valve closed and simultaneously maintaining the inlet passage open to permit fluid to flow from the source into the supply chamber, said control means controlling the rate of fluid pumped form the infusion pump by controlling the speed of the stepping motor to deliver a predetermined rate until a predetermined volume has been pumped from the pumping chamber, said control means subsequently closing the outlet and inlet passages with the outlet restriction valve and inlet valve while opening the intermediate passage and moving the piston assembly in the direction opposite the first direction so that fluid is drawn from the supply chamber to the pumping chamber to complete the pumping cycle.

* * * * *